(12) United States Patent
Weldon et al.

(10) Patent No.: US 12,075,968 B2
(45) Date of Patent: Sep. 3, 2024

(54) MEDICAL SYSTEMS, DEVICES, AND RELATED METHODS

(71) Applicant: Boston Scientific Scimed, Inc., Maple Grove, MN (US)

(72) Inventors: James Weldon, Newton, MA (US); Braeden Burns, Waterville, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/162,119

(22) Filed: Jan. 31, 2023

(65) Prior Publication Data
US 2023/0248361 A1 Aug. 10, 2023

Related U.S. Application Data

(60) Provisional application No. 63/307,235, filed on Feb. 7, 2022.

(51) Int. Cl.
| | | |
|---|---|---|
| *A61B 17/072* | (2006.01) | |
| *A61B 1/005* | (2006.01) | |
| *A61B 17/00* | (2006.01) | |

(52) U.S. Cl.
CPC ............ *A61B 17/072* (2013.01); *A61B 1/005* (2013.01); *A61B 2017/00398* (2013.01)

(58) Field of Classification Search
CPC ... A61B 1/00; A61B 1/00045; A61B 1/00066; A61B 1/00071; A61B 1/00096; A61B 1/00135; A61B 1/0676; A61B 1/015; A61B 1/05; A61B 1/018; A61B 1/005; A61B 1/0051; A61B 1/0052; A61B 1/0055; A61B 1/0057; A61B 2017/003; A61B 2017/00305; A61B 2017/07228; A61B 2017/00477; A61B 17/072; A61B 17/07207; A61B 17/115; A61B 17/0218; A61B 17/00234

USPC .......... 227/19, 175.1, 175.2, 176.1; 600/105, 600/131, 139, 140, 141, 142, 146, 152, 600/154, 172, 204; 606/49, 198

See application file for complete search history.

(56) References Cited

U.S. PATENT DOCUMENTS 5,704,898 A * 1/1998 Kokish .................. A61B 34/71
600/152
5,913,870 A * 6/1999 DeFonzo .......... A61B 17/00008
606/198

(Continued)

OTHER PUBLICATIONS

International Search Report and Written Opinion in PCT/US2023/061641 (13 pages).

*Primary Examiner* — Scott A Smith
(74) *Attorney, Agent, or Firm* — Bookoff McAndrews, PLLC (57) ABSTRACT

A medical system includes a first medical device and a second medical device. The first medical device includes a handle and a shaft. The shaft includes a lumen. A distal portion of the shaft includes an articulation joint, and the lumen extends through at least a portion of the articulation joint. The second medical includes a control device and a rod. The rod is configured to be positioned within at least a portion of the lumen of the shaft within the articulation joint. The control device is configured to control a position of the rod within the shaft. The position of the rod within the shaft controls an articulation angle of the articulation joint.

20 Claims, 7 Drawing Sheets

(56) References Cited

U.S. PATENT DOCUMENTS

| | | | |
|---|---|---|---|
| 6,142,994 A * | 11/2000 | Swanson | A61B 18/1492 |
| | | | 606/49 |
| 6,248,062 B1 * | 6/2001 | Adler | A61B 17/0218 |
| | | | 600/204 |
| 8,622,894 B2 | 1/2014 | Banik et al. | |
| 2005/0148820 A1 * | 7/2005 | Carrillo | A61M 25/02 |
| | | | 600/154 |
| 2005/0272975 A1 * | 12/2005 | McWeeney | A61B 1/307 |
| | | | 600/172 |
| 2007/0282167 A1 * | 12/2007 | Barenboym | A61B 1/0052 |
| | | | 600/131 |
| 2008/0064920 A1 | 3/2008 | Bakos et al. | |
| 2012/0172667 A1 * | 7/2012 | Takeuchi | A61B 1/0052 |
| | | | 600/140 |
| 2016/0174819 A1 * | 6/2016 | Ouyang | A61B 1/00098 |
| | | | 600/105 |
| 2017/0188793 A1 * | 7/2017 | Ouyang | A61B 1/015 |
| 2018/0160885 A1 | 6/2018 | Abitbol | |
| 2018/0325357 A1 | 11/2018 | Boulais | |
| 2019/0038270 A1 | 2/2019 | Thompson et al. | |
| 2019/0099062 A1 | 4/2019 | Ishihara et al. | |
| 2020/0359879 A1 | 11/2020 | Cahill et al. | |

* cited by examiner

MEDICAL SYSTEMS, DEVICES, AND RELATED METHODS

CROSS-REFERENCE TO RELATED APPLICATIONS

This application claims the benefit of priority under 35 U.S.C. § 119 from U.S. Provisional Application No. 63/307,235, filed Feb. 7, 2022, which is incorporated by reference herein in its entirety.

TECHNICAL FIELD

The present disclosure relates generally to medical systems, devices, and methods. In particular, this disclosure is directed to systems, devices, and methods for adjusting an articulation radius of an articulable or deflectable medical device.

BACKGROUND

Medical devices may include a handle and a shaft or insertion portion. The handle enables steering and physical manipulation of the shaft portion and may include controls for other operations of the device. A distal assembly may comprise part of the shaft portion and may have a plurality of channels or lumens for endoscopic operation. Often, instruments or tools may be inserted in a working channel in the shaft portion for performing a therapeutic or diagnostic procedure. The shaft or insertion portion may be articulated or deflected, for example, via one or more actuators on the handle. The articulation or deflection may include a predetermined angle of articulation or deflection and/or a predetermined responsiveness to movement of the one or more actuators. However, different procedures and/or different cavities within a patient may require different maneuvers, different responsiveness to movement of the one or more actuators, and/or different articulation or deflection radii. Therefore, a need exists for shafts or insertion portions of endoscopic devices to have variable articulation or deflection radii and/or other controls.

SUMMARY

According to an example, a medical system may include a first medical device and a second medical device. The first medical device may include a handle and a shaft. The shaft may include a lumen. A distal portion of the shaft may include an articulation joint, and the lumen may extend through at least a portion of the articulation joint. The second medical device may include a control device and a rod. The rod may be selectively positionable within at least a portion of the lumen of the shaft within the articulation joint. The control device may be configured to control a position of the rod within the shaft. The position of the rod within the shaft may control an articulation angle of the articulation joint.

The medical system may include one or more of the following aspects. The control device may be integrated in or coupled to a portion of the handle. The control device may include a slider, a pin coupled to the slider, and a track positioned within a distal portion of the handle. Movement of the pin within the track may control the position of the rod within the lumen of the shaft. The track may include a central channel, a plurality of slots extending from the central channel, and a plurality of grooves extending from the slots. A spacing of the slots along the central channel may correspond to a length of one or more links in the articulation joint.

The control device may include a dial, a dowel extending from the dial, and a pinion coupled to the dowel. The rod may be coupled to a rack. Rotational movement of the dial may actuate a linear movement of the rack to control the position of the rod within the shaft. The rack may include a plurality of teeth. A spacing of the teeth on the rack may correspond to a length of one or more links in the articulation joint.

The control device may include a screw coupled to the rod and a coupler. The screw may include a threading. The coupler may include an internal threading. The rod may be coupled to a distal end of the screw. Rotational movement of the screw may control the position of the rod within the shaft.

The control device may include a primary wheel, one or more secondary wheels, and a mounting element. The mounting element may be coupled to a distal portion of the handle. Rotational movement of the primary wheel or the one or more secondary wheels may control the position of the rod within the shaft.

The articulation joint may include nine articulation links. Each articulation link may provide for 25 degrees of articulation. The rod may be less flexible than the articulation joint. The articulation joint may include a plurality of articulation links. More distal articulation links may provide for greater articulation than more proximal articulation links. The handle may include an instrument port on a distal portion of the handle configured to receive the rod and to guide the rod into the lumen of the shaft. The first medical device may include an articulation lever positioned on a portion of the handle. The articulation lever may be connected to the articulation joint via one or more articulation wires.

In another example, a medical device may include a rod and a control device coupled to a proximal portion of the rod. The control device may include one or more control members. Movement of the one or more control members in a first direction may advance the rod distally. Movement of the one or more control members in a second direction may retract the rod proximally. The control device may include one or more indications indicative of a position of the rod relative to the control device.

The medical device may include one or more of the following aspects. The control device may include a slider, a pin coupled to the slider, and a track. The track may include a central channel, a plurality of slots extending from the central channel, and a plurality of grooves extending from the slots and forming the indications. Movement of the pin within the track may control the position of the rod relative to the control device. The control device may include a dial, a dowel extending from the dial, and a pinion coupled to the dowel. The rod may be coupled to a rack. The rack may include a plurality of teeth. A spacing of the teeth on the rack may correspond to a length of one or more links in the articulation joint. Rotational movement of the dial may actuate a linear movement of the rack to control the position of the rod relative to the control device.

In yet another example, a method may include delivering a first medical device to a treatment site. The first medical device may include a handle and a shaft, and the shaft may include an articulation joint at a distal end of the shaft. The method may include manipulating a distal portion of the first medical device. Manipulating the distal portion of the first medical device may include manipulating an actuation lever on the handle to articulate the articulation joint by a first articulation angle. The method may also include delivering a second medical device to the treatment site. The second medical device may include a control device and a rod, and delivering the second medical device to the treatment site may include delivering a portion of the rod through a port of the handle and through a lumen of the shaft to the articulation joint. The method may further include positioning the second medical device relative to the first medical device. The method may also include manipulating the distal portion of the first medical device. Manipulating the distal portion of the first medical device may include manipulating the actuation lever on the handle to articulate the articulation joint by a second articulation angle that is smaller than the first articulation angle.

The method may include one or more of the following aspects. The control device may include a slider, a pin coupled to the slider, and a track. The track may include a central channel and a plurality of slots extending from the central channel. Positioning the second medical device relative to the first medical device may include manipulating the slider to move the pin within the track to control the position of the rod relative to the control device and the shaft of the first medical device.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Examples of this disclosure include systems, devices, and methods for facilitating and/or improving the efficacy, efficiency, cost, and/or safety of a medical procedure. Embodiments of the disclosure may relate to systems, devices, and methods for performing various medical procedures and/or treating portions of the larynx, trachea, bronchi (primary bronchi), lobar (secondary bronchi), segmental (tertiary bronchi), bronchiore, terminal bronchiore, or any other portion of the respiratory system. Additionally, embodiments of the disclosure may relate to systems, devices, and methods for performing various medical procedures and/or treating portions of the large intestine (colon), small intestine, cecum, esophagus, stomach, or any other portion of the gastrointestinal tract. Furthermore, embodiments of the disclosure may relate to systems, device, and methods for performing various medical procedures and/or treating portions of the kidneys, ureters, bladder, urethra, or any other portion of the urinary tract. In these aspects, the systems, devices, and methods discussed herein may be used to treat any other suitable patient anatomy (collectively referred to herein as a "treatment site").

Various embodiments described herein include single-use or disposable medical devices. Some aspects of the disclosure may be used in performing an endoscopic, arthroscopic, bronchoscopic, ureteroscopic, colonoscopic, or other type of procedure. For example, the disclosed aspects may be used as or with duodenoscopes, bronchoscopes, ureteroscopes, colonoscopes, catheters, diagnostic or therapeutic tools or devices, or other types of medical devices. One or more of the elements discussed herein could be metallic, plastic, or include a shape memory metal (such as nitinol), a shape memory polymer, a polymer, or any combination of biocompatible materials.

Reference will now be made in detail to examples of the disclosure described above and illustrated in the accompanying drawings. Wherever possible, the same reference numbers will be used throughout the drawings to refer to the same or like parts. It is noted that one or more aspects of the medical systems, devices, and methods discussed herein may be combined and/or used with one or more aspects of other medical systems, devices, and methods discussed herein.

Figure 1:
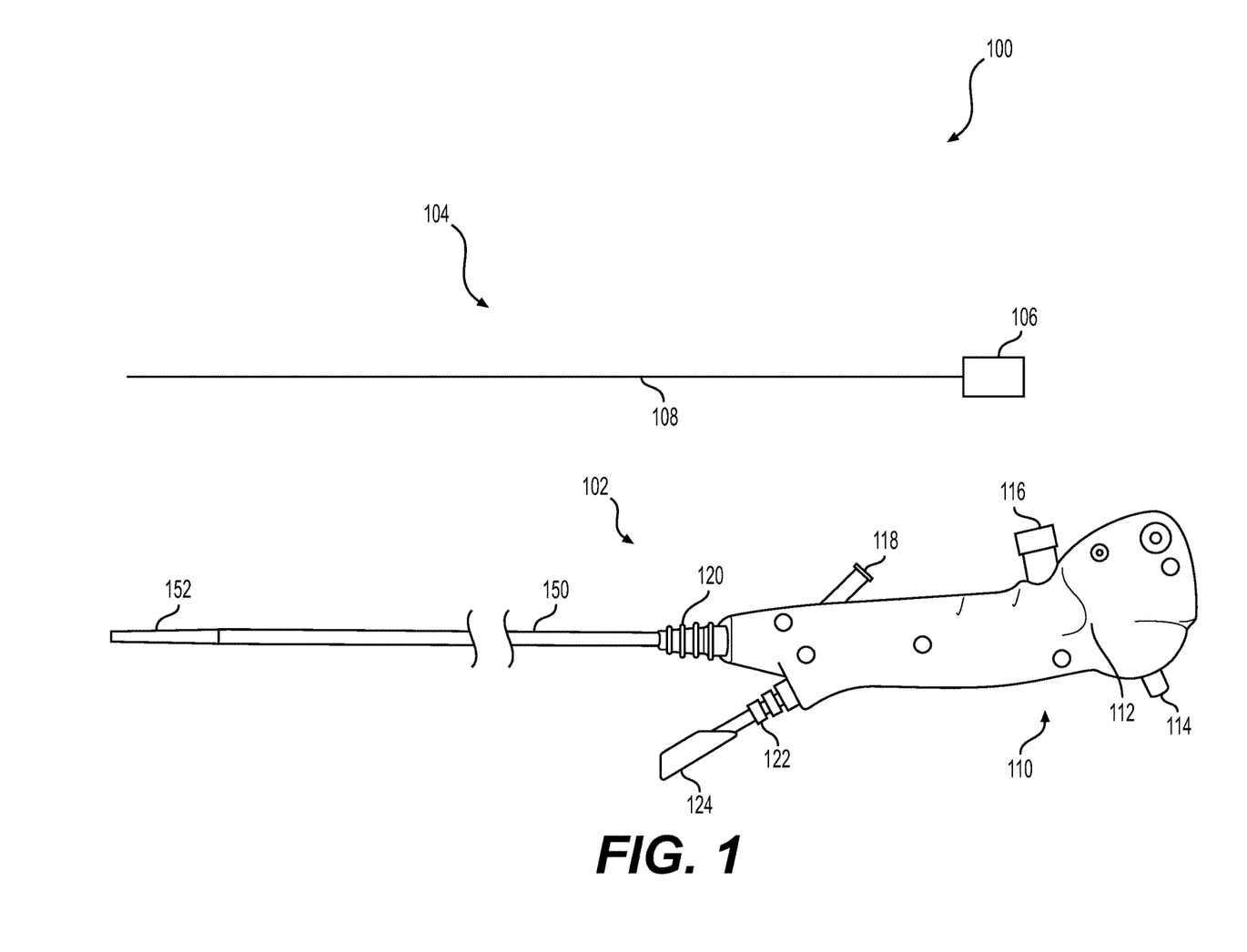
FIG. 1 illustrates a side view of an exemplary medical system, including a first medical device and a second medical device, according to aspects of this disclosure.

FIG. 1 depicts a medical system ("system") 100. System 100 may include a first medical device 102 and a second medical device 104. First medical device 102 may be referred to herein as an endoscope, but it should be appreciated that first medical device 102 may be an endoscope, duodenoscope, bronchoscope, ureteroscope, colonoscope, catheter, or other type of medical device. As discussed in detail below, second medical device 104 may be delivered through one or more portions of first medical device 102, for example, to help control an articulation or deflection radius or other features of a distal portion of first medical device 102

Figure 2A:
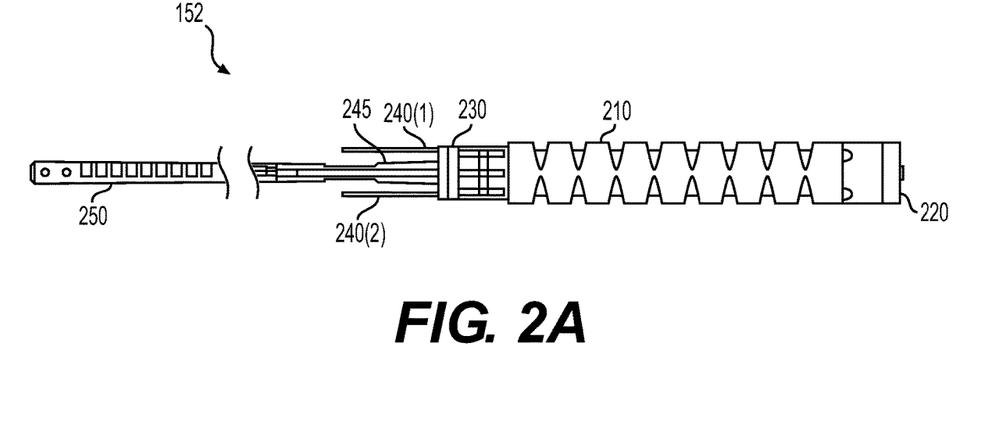
FIGS. 2A and 2B illustrate a side view and a perspective view of a distal assembly portion with an articulation joint of the first medical device.
Figure 2B:
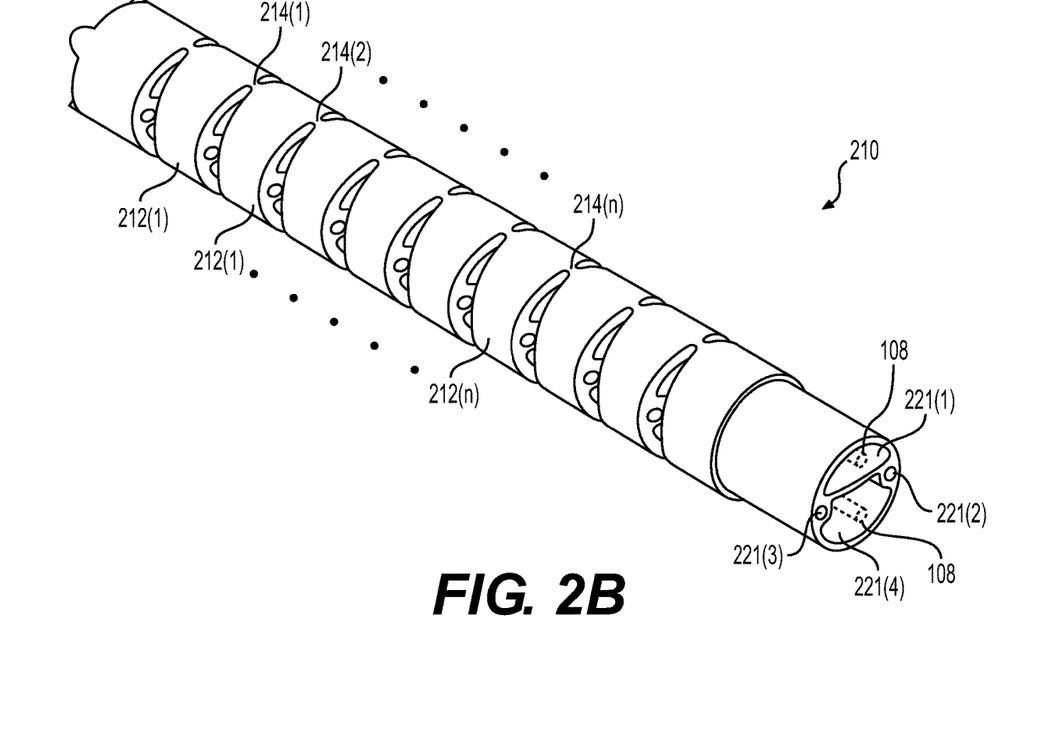
Figure 3A:
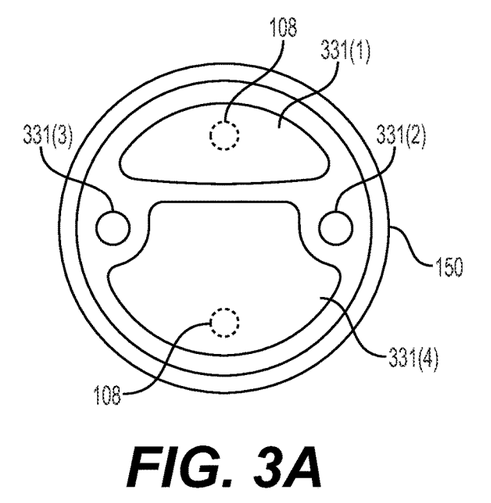
FIGS. 3A and 3B illustrate a cross-sectional view of the distal assembly portion of the first medical device.
Figure 3B:
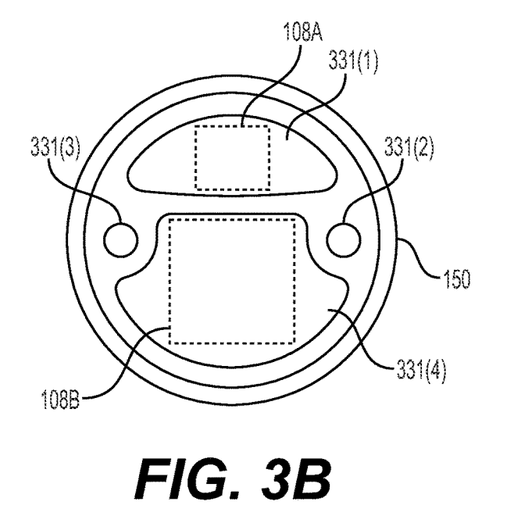
Figure 3C:
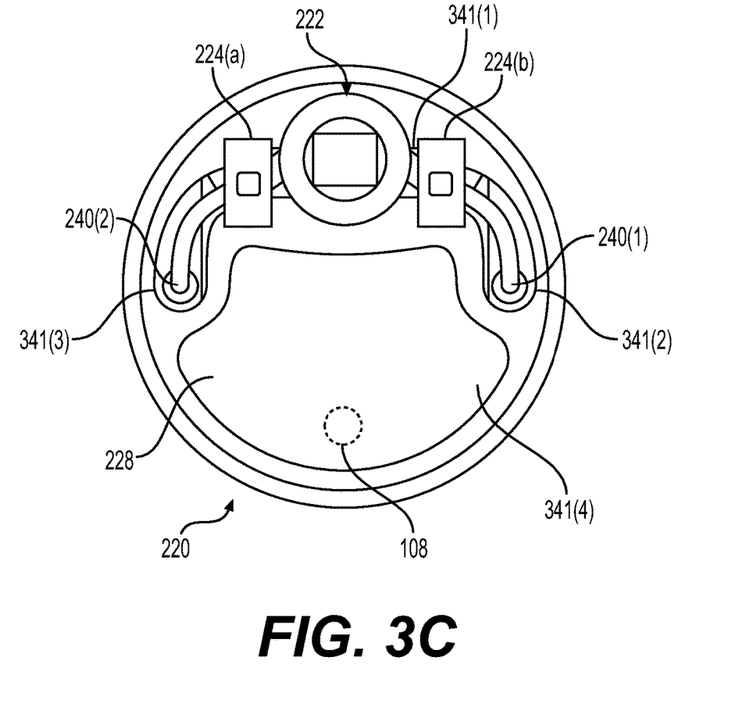
FIG. 3C illustrates an end view of a distal cap of the distal assembly of the first medical device.

First medical device 102 includes a handle portion ("handle") 110 and a shaft/insertion portion ("shaft") 150. Handle 102 may include one or more of a gripping surface 112, an articulation lever 114, a suction port 116, an instrument or irrigation port ("instrument port") 118, a shaft strain relief portion 120, an umbilicus strain relief portion 122, and an umbilicus 124 (the proximal portion of which is shown in FIG. 1). A distal end of shaft 150 may connect to or include a distal assembly 152. Distal assembly 152 may include an articulation joint 210 and a distal cap 220 (FIGS. 2A, 2B, and 3C). Distal assembly 152 may include one or more other devices and/or may be configured to receive other devices, such as a camera or light illuminating or illumination elements (e.g., light emitting diodes or "LEDs"). As described herein, first medical device 102 has a working channel that extends from distal cap 220 of distal assembly 152, through articulation joint 210 and shaft 150, to instrument port 118 of handle 110. The working channel of first medical device 102 thus may be a combination of a working channel of distal cap 220, a working channel of articulation joint 210, and a working channel of shaft 150, as described in detail herein.

Gripping surface 112 of the handle 110 may help to enable physical handling of system 100 (e.g., first medical device 102), for example, by a medical professional or other operator. Articulation lever 114 may be configured to be manipulated, and when articulation lever 114 is manipulated by an operator, articulation lever 114 may articulate articulation joint 210 of first medical device 102 in a plane, for example, in an up/down direction. As discussed below, articulation joint 210 may articulate through a range of approximately 180 degrees, approximately 200 degrees, approximately 225 degrees, etc. Suction port 116 may be a valve configured to provide air and/or water suction (e.g., through a working channel of first medical device 102). Instrument port 118 may be used for passing medical instruments (e.g., a portion of second medical device 104) or other tools and devices through the working channel of first medical device 102. In one example, as described herein, the working channel of first medical device 102 may be a tubeless working channel (e.g., an open channel without an additional tube inserted for guiding an inserted tool). The working channel may have a large cross-sectional area for receiving medical instruments and other tools and devices.

Shaft strain relief 120 may be configured to interface with shaft 150 of first medical device 102. Umbilicus 124 may be connected to umbilicus strain relief portion 122, and may be configured to extend from handle 110, for example, for connection to an external device (e.g., a controller, computing device, processor, display device, user interface, etc.). For example, umbilicus 124 may be used to connect first medical device 102 to components to provide optical controls of first medical device 102, for example, including a camera, video, light, etc. Shaft 150 may be configured to be inserted into a patient for medical treatment (e.g., via one or more orifices of a patient's body).

Second medical device 104 includes a control device 106 and a mandrel or rod ("rod") 108. Rod 108 may be delivered through handle 110 and/or shaft 150, for example, through a working channel to distal assembly 152. Control device 106 may control a position of rod 108. For example, control device 106 may be coupled to and/or positioned adjacent to handle 110. As discussed below, control device 106 may be integrated in and/or coupled to handle 110. Alternatively, control device 106 may be separate from handle 110. Manipulation of control device 106 may control a position of rod 108 relative to shaft 150 and/or distal assembly 152. For example, manipulation of control device 106 may linearly adjust a position of rod 108 relative to shaft 150 and/or distal assembly 152. In these aspects, the position of rod 108 relative to shaft 150 and/or distal assembly 152 may control the articulation or deflection angle, for example, when articulation lever 114 is manipulated. For example, rod 108 may have a rigidity that is more rigid than a rigidity of distal assembly 152. Stated another way, rod 108 may have a flexibility that is less flexible than a flexibility of distal assembly 152. In these aspects, rod 108 may be a stiffening element to increase the stiffness of distal assembly 152. Alternatively, rod 108 may have a flexibility that is a similar flexibility of distal assembly 152. In one or more of these aspects, rod 108 may be smaller than the lumen through which rod 108 extends (FIG. 3A). Alternatively, in one or more of these aspects, rod 108 may be larger, for example, approximating the size of the lumen through which rod 108 extends (FIG. 3B). As discussed below, the amount of space between the exterior of rod 108 and the interior walls of the lumen through which rod 108 extends may help to control the effect that rod 108 has on the articulation of distal assembly 152.

As discussed in detail below, with rod 108 in a first configuration (e.g., a proximally retracted position), manipulation of articulation lever 114 may articulate or deflect a distal portion of shaft 150 or distal assembly 152 by a first angle. With rod 108 in a second configuration (e.g., a distally extended position), manipulation of articulation lever 114 may articulate or deflect the distal portion of shaft 150 or distal assembly 152 by a second angle, for example, a smaller angle than the first angle. In these aspects, rod 108 may be selectively movable to control the articulation or deflection angle of the distal end of shaft 150 or distal assembly 152.

FIG. 2A illustrates a side view of distal assembly 152 and certain electronics that extend through shaft 150 and umbilicus 124, and FIG. 2B illustrates a perspective view of a portion of distal assembly 152. Distal assembly 152 comprises an articulation joint 210, distal cap 220, a plurality of cables and wires 245, e.g., for connections to a camera and LEDs, a Bowden disk 230, and two articulation wires 240(1) and 240(2). The cables and wires 245 within distal assembly 152 extend through shaft 150 and umbilicus 124 to a circuit board 250. Circuit board 250 may be at an end of umbilicus 124 that connects to the external controller. Alternatively, circuit board 250 may be positioned on or within handle 110, a remote processor, umbilicus, etc. Thus, the circuit board 250 is not part of distal assembly 152 itself, but is configured for connections to the LED wires and the camera cables disposed through distal assembly 152.

In general, articulation joint 210 may include multiple lumens (FIG. 2B). These lumens may operate as tubeless working channels for articulation joint 210, lumen(s) to receive articulation wires 240(1) and 240(2), and lumen(s) to receive wires for the LEDs/camera. Similarly, shaft 150 is positioned between handle 110 and distal assembly 152, and shaft 150 also may include multiple lumens that may operate as a tubeless working channel for shaft 150, lumen(s) to receive articulation wires 240(1) and 240(2), and lumen(s) to receive wires for the LEDs/camera.

Distal cap 220 of distal assembly 152 may include a camera and one or more LEDs, for example, two LEDs. Further details of distal cap 220 are discussed in connection with FIGS. 3A-3C below. Distal cap 220 may be attached to a distal end of articulation joint 210. A cable for the camera, as well as two sets of one or more wires for each of the respective LEDs may pass through distal cap 220 and articulation joint 210. The camera cable may include multiple wires that are held together by a wire harness. Bowden disk 230 may be attached to the proximal end of articulation joint 210. Articulation wires 240(1) and 240(2) may extend from handle 110, for example, from articulation lever 114 (not shown in FIG. 2) through shaft 150 and articulation joint 210 for controlling movement of articulation joint 210, for example, in an up or down direction.

FIG. 2B shows a perspective view of articulation joint 210, with distal cap 220 removed. It is noted that FIG. 2B illustrates articulation joint 210 without any wires passing through lumens 221(1)-221(4). Articulation joint 210 may be a single-piece element, for example, that is formed of injection-molded polypropylene or another appropriate material and/or formation process. The thickness of the outer walls of articulation joint 210 may taper, so as to provide greater strength at a proximal end of articulation joint 210 (e.g., the wall is thinner at the distal end) and/or increased flexibility at a distal end of articulation joint 210. Articulation joint 210 includes multiple links, shown at reference numerals 212(1)-212(n). Links 212(1)-212(n) are connected by hinge portions 214(1)-214(n).

In one aspect, articulation joint 210 may include nine links 212. Each link 212 may provide up to approximately 25 degrees of mobility. Accordingly, nine links 212 may all for articulation joint 210 to articulate more than approximately 180 degrees, for example, up to approximately 225 degrees. Alternatively, distal links may provide for a greater degree of mobility than proximal links. In this aspect, positioning rod 108 within one or more of the distal links may distribute the load on articulation joint 210 from articulation wires 240 to more flexible distal links. As discussed in detail below, rod 108 may be incrementally positioned within one or more links 212 of articulation joint 210 to prevent the one or more links 212 from articulating, and thus adjusting the articulation radius of articulation joint 210. The adjusted articulation radius of articulation joint 210 may allow the user to articulate or deflect distal assembly 152 through a smaller articulation radius, for example, for or more precise adjustments with less sensitivity to movements of articulation lever 114. Furthermore, in some aspects, articulation joint 210 may be encased with a thin polyurethane cover.

Articulation joint 210 may be part of distal assembly 152. Articulation joint 210 may include a number of lumens, for example, four lumens 221(1)-221(4). For example, first lumen 221(1) of articulation joint 210 may be configured to receive cables and wires 245 for connection to camera 222 and LEDs 224(a) and 224(b) (described in connection with FIG. 2A, above). In one example, first lumen 221(1) may receive a wire for each of LEDs 224(a) and 224(b) and one cable for the camera 222 (e.g., the cable may comprise multiple wires for the camera 222 that are held together with the wires for LEDs 224(a) and 224(b) using a wire harness). Second lumen 221(2) of articulation joint 210 may receive articulation wire 240(1) to connect with articulation lever 114, and third lumen 221(3) of articulation joint 210 may receive articulation wire 240(2) to connect with articulation lever 114. As mentioned above, articulation lever 114 of handle 110 may be configured to adjust articulation wires 240(1) and 240(2) for articulation in one plane (e.g., up/down). For example, moving articulation lever 114 in one direction pulls on one articulation wire to move in the "left" direction, and moving articulation lever 114 in another direction pulls on another articulation wire to move in the "right" direction. Additionally or alternatively, if articulation joint 210 is oriented in a different direction (e.g., rotated 90 degrees), then moving articulation lever 114 in one direction pulls on one articulation wire to move in the "up" direction, and moving articulation lever 114 in another direction pulls on another articulation wire to move in the "down" direction Fourth lumen 221(4) of articulation joint 210 may be utilized as the working channel for articulation joint 210. The working channel of articulation joint 210 may be part of the working channel for first medical device 102 (together with the working channel for the distal cap 220 and the working channel for shaft 150, described in more detail herein).

FIGS. 3A and 3B depict lateral cross-sectional views of shaft 150, and FIG. 3C depicts an end view of distal cap 220. As mentioned above, shaft 150 may include a number of lumens. In one aspect, shaft 150 may include four lumens 331(1)-331(4). For example, first lumen 331(1) of shaft 150 may be configured to receive cables and wires 245 for connection to camera 222 and LEDs 224(a) and 224(b) (described in connection with FIG. 2A, above). In one example, first lumen 331(1) may receive a wire for each of LEDs 224(a) and 224(b) and one cable for the camera 222 (e.g., the cable may comprise multiple wires for the camera 222 that are held together with the wires for LEDs 224(a) and 224(b) using a wire harness). Second lumen 331(2) of shaft 150 may receive articulation wire 240(1) to connect with articulation lever 114, and third lumen 331(3) of shaft 150 may receive articulation wire 240(2) to connect with articulation lever 114. Fourth lumen 331(4) of shaft 150 may be utilized as the working channel for shaft 150. The working channel of shaft 150 may be part of the working channel for first medical device 102 (together with the working channel for the distal cap 220 and the working channel for articulation joint 210).

As shown in FIG. 3C, distal cap 220 includes one or more of a camera 222, one or more LEDs, for example, two LEDs 224(a) and 224(b) on opposite sides of camera 222, articulation wires 240(1) and 240(2), and an opening 228 (e.g., an opening for a tubeless working channel). It should be appreciated that articulation wires 240(1) and 240(2) are two separate wires, though they are shown in FIG. 3B as forming a continuous loop.

Distal cap 220 has four lumens, shown at reference numerals 341(1)-341(4) in FIG. 3C. Camera 222 and LEDs 224(a) and 224(b) may be positioned in a first lumen (e.g., lumen 341(1)), which may at least partially align with lumen 331(1) of shaft 150 and lumen 221(1) of articulation joint 210. Articulation wire 240(1) may be positioned in a second lumen (e.g., lumen 341(2)), and articulation wire 240(2) may be positioned in a third lumen (e.g., lumen 341(3)). Second lumen 341(2) may at least partially align with lumen 331(2) of shaft 150 and lumen 221(2) of articulation joint 210. Third lumen 341(3) may at least partially align with lumen 331(3) of shaft 150 and lumen 221(3) of articulation joint 210. A fourth lumen (e.g., lumen 341(4)) may be utilized for a tubeless working channel of distal cap 220. Fourth lumen 341(4) may at least partially align with lumen 331(4) of shaft 150 and lumen 221(4) of articulation joint 210. As described herein, the working channel of distal cap 220 may interface with the working channel of articulation joint 210 and the working channel of shaft 150 to comprise the working channel of first medical device 102. Lumens 341(1), 341(2), and 341(3) of distal cap 220 may be separate or may be in communication, for example, forming an approximately C-shaped opening in a distal end of distal cap 220.

As mentioned above, a portion of second medical device 104 may be inserted through and/or coupled to first medical device 102. Rod 108 may be delivered through a portion of handle 110 and through a portion of shaft 150 and/or distal assembly 152. For example, rod 108 may be delivered through instrument port 118 and through a portion of shaft 150 and/or distal assembly 152. Delivering rod 108 through instrument port 118 may guide rod 108 into one or more lumens of shaft 150, articulation joint 210, and/or distal cap 220. For example, delivering rod 108 through instrument portion 118 may guide a portion of rod 108 into first lumen 331(1) of shaft 150 (FIGS. 3A and 3B). Extending rod 108 distally may also deliver a portion of rod 108 into first lumen 221(1) of articulation joint 210 (FIG. 2B). Further extending rod 108 distally may also deliver a portion of rod 108 into first lumen 341(1) of distal cap 220, for example, where camera 222 and/or LEDs 224(*a*), 224(*b*) are positioned.

Alternatively, delivering rod 108 through instrument port 118 may guide a portion of rod 108 into fourth lumen 331(4) of shaft 150 (FIGS. 3A and 3B). Extending rod 108 distally may also deliver a portion of rod 108 into fourth lumen 221(4) of articulation joint 210 (FIG. 2B). Further extending rod 108 distally may also deliver a portion of rod 108 into fourth lumen 341(4) of distal cap 220 (FIG. 3C). A user may control the position of rod 108 with control device 106, for example, with control device 106 being coupled to first medical device 102 (e.g., to handle 110) and/or remaining positioned outside of first medical device 102. In these aspects, delivering rod 108 through instrument port 118 may position rod 108 within the camera lumen of first medical device 102, or within the working channel of first medical device 102. Additionally, the extension of rod 108 relative to first medical device 102 (e.g., relative to articulation joint 210) may control the articulation or deflection of distal assembly 152 of first medical device 102.

As mentioned above, one or more rods 108 may be differently sized relative to the lumen through which the one or more rods 108 extends. For example, as shown in FIG. 3A, rod 108 may be cylindrical (i.e., with a circular cross-section) and be smaller than lumen 331(1) or lumen 331(4). Alternatively, as shown in FIG. 3B, rods 108A, 108B may be a rectangular prism (i.e., with a rectangular cross-section). Rods 108A, 108B may be sized to fit within one or more of lumen 331(1) or lumen 331(4), for example, approximating the size and/or approximately abutting or nearly abutting the interior of lumen 331(1) or lumen 331(4). In one or more aspects, rod 108A may be sized to fit within lumen 331(1), and rod 108B may be sized to fit within lumen 331(4), for example, larger than rod 108A. As mentioned above, the amount of space between the exterior of rods 108A, 108B and the interior walls of lumens 331(1), 331(4) through which rod 108 extends may help to control the effect that rod 108 has on the articulation of distal assembly 152. For example, more space between rods 108A, 108B and the interior walls of lumens 331(1), 331(4) may correspond to a greater amount of articulation when rods 108A, 108B are positioned within lumens 331(1), 331(4). On the other hand, less space between rods 108A, 108B and the interior walls of lumens 331(1), 331(4) may correspond to a lesser amount of articulation when rods 108A, 108B are positioned within lumens 331(1), 331(4).

Although not shown, in some aspects, rod 108 may be otherwise coupled to first medical device 102. Although the above discussion discloses rod 108 extending through one or both of the working lumen and/or the camera lumen of first medical device 102, this disclosure is not so limited. For example, one or more of shaft 150, distal assembly 152 (including articulation joint 210), and/or distal cap 220 may include separate lumens to movably receive rod 108. In another example rod 108 may be coupled (e.g., via an adhesive) adjacent to an exterior of shaft 150 and/or distal assembly 152, without extending through a lumen of first medical device 102. Furthermore, although not shown, rod 108, 108A, 108B may be tapered, stepped, and/or have a profile on a distal end or distal portion of rod 108, 108A, 1086, which may help to minimize, reduce, or otherwise control the deflection articulation links 212. For example, a proximal portion of rod 108, 108A, 108B may be wider or otherwise larger than a distal portion of rod 108, 108A, 108B. In this aspect, the articulation links 212 through which the proximal portion of rod 108, 108A, 108B extends may articulate less than the articulation links 212 through which the distal portion of rod 108, 108A, 108B extends. Furthermore, extending rod 108, 108A, 108B through lumen 331(1) (i.e., a camera lumen) may control the deflection of shaft 150 to a greater extent than inserting rod 108, 108A, 108B through lumen 331(4) (i.e., a working channel lumen). As discussed above, lumen 331(1) (i.e., a camera lumen) may be smaller than lumen 331(4) (i.e., a working channel lumen), so there may be less space surrounding rod 108, 108A, 108B when rod 108, 108A, 108B is within lumen 331(1) than when rod 108, 108A, 108B is within lumen 331(4). As a result, distal assembly 152 may be able to deflect to less of an extent when rod 108, 108A, 108B is within lumen 331(1) than when rod 108, 108A, 108B is within lumen 331(4).

FIGS. 4A-4E illustrate different articulations of distal assembly 152, for example, with various configurations of second medical device 104 (i.e., rod 108) relative to first medical device 102. As discussed below, the position of rod 108 within first medical device 102 may control (e.g., limit and/or reduce) the articulation or deflection of distal assembly 152 of first medical device 102 and/or the sensitivity of distal assembly 152 in response to movement of articulation lever 114.

Figure 4A:
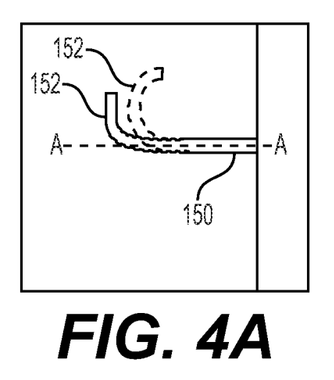
FIGS. 4A-4E illustrate various deflections or articulations of a distal portion of the distal assembly portion under various conditions.
Figure 4B:
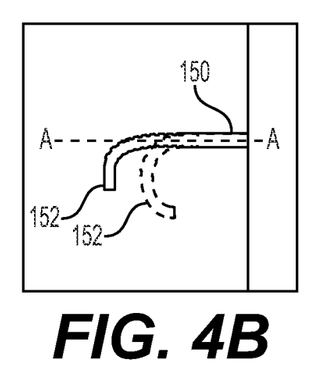

FIGS. 4A and 4B illustrate aspects of system 100 with rod 108 inserted through the working lumen of first medical device 102, for example, through fourth lumen 331(4) of shaft 150, fourth lumen 221(4) of articulation joint 210 of distal assembly 150, and/or fourth lumen 341(4) of distal cap 220. FIGS. 4A and 4B illustrate distal assembly 152 being deflected, for example, via articulation lever 114 (FIG. 1), with and without rod 108 inserted through the working lumen of first medical device 102. Specifically, FIGS. 4A and 4B illustrate distal assembly 152 being deflected (e.g., up and down, respectively) without rod 108 inserted, as shown in the dashed line version of distal assembly 152. In this configuration, as shown, distal assembly 152 may deflect between approximately 135 and approximately 225 degrees, for example, approximately 180 degrees, either upwards or downwards, relative to a longitudinal axis A of shaft 150. Furthermore, FIGS. 4A and 4B illustrate distal assembly 152 being deflected (e.g., up and down, respectively) with rod 108 inserted (e.g., through at least a portion of articulation joint 210), as shown in the solid line version of distal assembly 152. In this configuration, distal assembly 152 may deflect between approximately 60 and approximately 120 degrees, for example, approximately 90 degrees, either upwards or downwards, relative to the longitudinal axis A of shaft 150. It is noted that, as discussed below, the distance which rod 108 is inserted through articulation joint 210 (i.e., the position of the distal end of rod 108 relative to links 212(1)-212(n) of articulation joint 210) may also control the articulation angle of articulation joint 210.

Figure 4C:
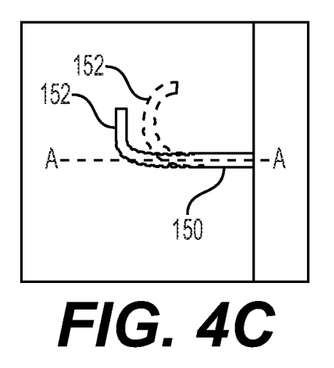
Figure 4D:
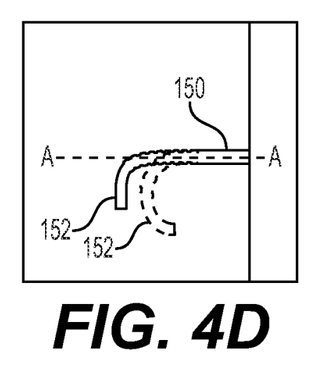

FIGS. 4C and 4D illustrate aspects of system 100 with rod 108 inserted through the camera lumen of first medical device 102, for example, through first lumen 331(1) of shaft 150, first lumen 221(1) of articulation joint 210 of distal assembly 150, and/or first lumen 341(1) of distal cap 220. FIGS. 4C and 4D illustrate distal assembly 152 being deflected, for example, via articulation lever 114 (FIG. 1), with and without rod 108 inserted through the working lumen of first medical device 102. Specifically, FIGS. 4C and 4D illustrate distal assembly 152 being deflected (e.g., up and down, respectively) without rod 108 inserted, as shown in the dashed line version of distal assembly 152. In this configuration, as shown, distal assembly 152 may deflect between approximately 135 and approximately 225 degrees, for example, approximately 180 degrees, either upwards or downwards, relative to the longitudinal axis A of shaft 150. Furthermore, FIGS. 4C and 4D illustrate distal assembly 152 being deflected (e.g., up and down, respectively) with rod 108 inserted (e.g., through at least a portion of articulation joint 210), as shown in the solid line version of distal assembly 152. In this configuration, distal assembly 152 may deflect between approximately 60 and approximately 120 degrees, for example, approximately 90 degrees, either upwards or downwards, relative to the longitudinal axis A of shaft 150. Furthermore, it is noted that, as discussed below, the distance which rod 108 is inserted through articulation joint 210 (i.e., the position of the distal end of rod 108 relative to links 212(1)-212(n) of articulation joint 210) may also control the articulation angle of articulation joint 210. As mentioned above, inserting rod 108, 108A, 108B through lumen 221(1) (i.e., a camera lumen) may control or affect the deflection of articulation joint 210 to a greater extent than inserting rod 108, 108A, 108B through lumen 221(4) (i.e., a working channel lumen).

As mentioned, the distal extension of rod 108 within the working lumen or the camera lumen of first medical device 102 may further control the deflection angle of distal assembly 152. For example, extending rod 108 further distally (i.e., through a larger number of links 212 of articulation joint 210) may further limit the deflection angle of distal assembly 152, while retracting rod 108 proximally (i.e., through a smaller number of links 212 of articulation joint 210) may allow distal assembly 152 to deflect at a larger angle. Furthermore, in one or more aspects, two or more rods 108 may be delivered through the first medical device 102, for example, with one rod being delivered through the working lumen, and another rod being delivered through the camera lumen. In this aspect, the rods may be selectively extended and/or retracted to control a deflection of distal assembly 152 and distal portion of first medical device 102.

Figure 4E:
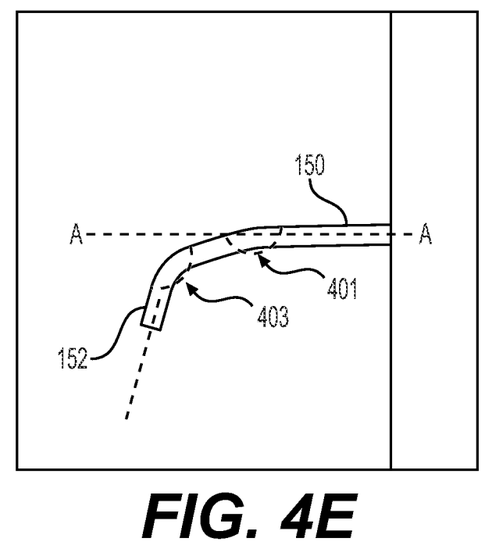

FIG. 4E illustrates a partial extension of rod 108 through the working lumen or the camera lumen of first medical device 102. In this aspect, distal assembly 152 may include two deflection points 401 and 403. For example, distal assembly 152 may include a first deflection angle relative to the longitudinal axis A of shaft 150 at deflection point 401. Deflection point 401 may be formed by the connection of distal assembly 152 and shaft 150, with distal assembly 152 including articulation joint 210 (not shown). Deflection point 403 may be formed by the remainder of distal assembly 152, through which rod 108 does not extend. Alternatively, distal assembly 152 may include one deflection point (i.e., deflection point 403), for example, formed by the transition between the portion of distal assembly 152 through which rod 108 extends and the portion of distal assembly 152 through which rod 108 does not extend.

Figures 5A, 5B:
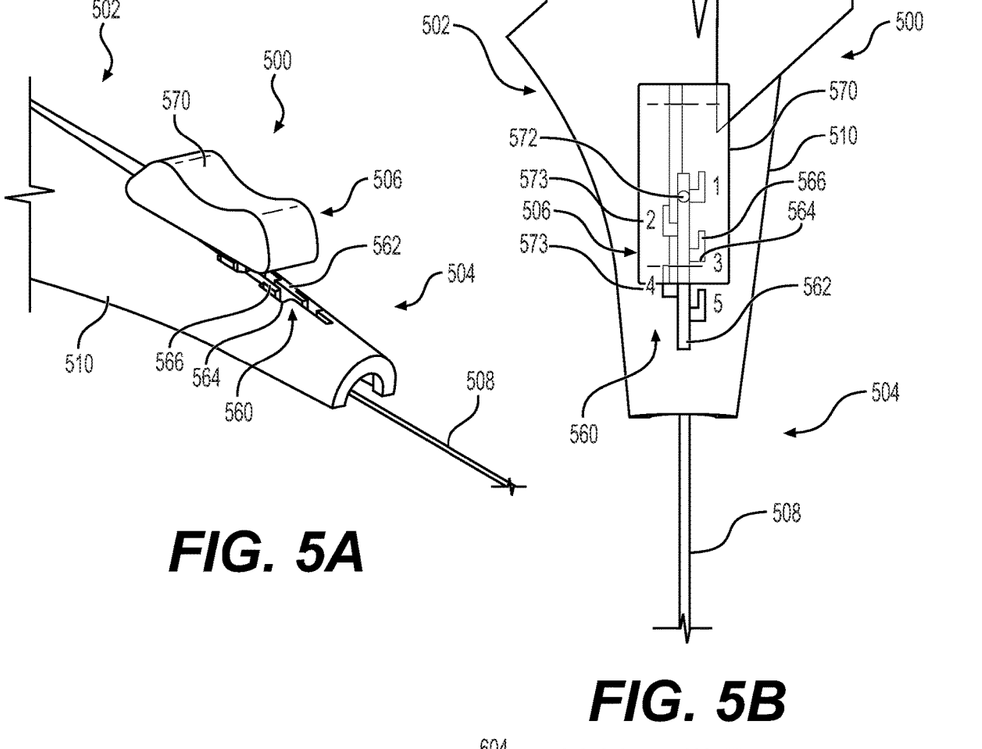
FIGS. 5A and 5B illustrate a perspective view and a top view, respectively, of another embodiment of the second medical device.

FIGS. 5A and 5B illustrate a portion of another system 500, with elements similar to system 100 shown with 400 added to the element number. System 500 includes a first medical device 502 and a second medical device 504. As discussed above, first medical device 502 includes a handle 510 and a shaft (not shown). Second medical device 504 includes a control device 506 and a rod 508. In this aspect, control device 506 may be coupled to and/or movable relative to handle 510.

For example, handle 510 may include one or more tracks 560, for example, one track 560, in a distal portion of handle 510. Track 560 may include a central channel 562 and a number of slots 564. Central channel 562 may extend substantially parallel to a longitudinal axis of first medical device 502 and/or handle 510. Slots 564 may extend laterally from track 560, for example, regularly spaced and alternatingly extending from different sides of track 560. Additionally, slots 564 may include grooves 566. Grooves 566 may extend from slots 564, for example, parallel to central channel 562. In one aspect, handle 510 may be formed of two halves, such that coupling the two halves forms track 560.

Control device 506 may include a slider 570. Slider 570 may be movably positioned adjacent to handle 510. For example, slider 570 may include a pin 572 that extends at least partially into an interior portion to handle 510, and pin 572 may be movable within track 560. For example, manipulation of slider 570 relative to handle 510 (e.g., with an operator's thumb or another figure) may manipulate pin 572 within track 560. Pin 572 may be advanced distally or retracted proximally, for example, within central channel 562 to control the distal extension or proximal retraction of rod 508, for example, within the distal assembly (not shown). Additionally, pin 572 may be positioned within one or more slots 564 and/or grooves 566, for example, to help secure the position of slider 570 and pin 572 relative to handle 510 and track 560, and thus help to secure the position of rod 508 relative to the distal assembly (not shown).

Although not shown, pin 572 may be coupled to a drive element, for example, internal to handle 510, and the drive element may help to secure slider 570 to handle 510. The drive element may also help to couple slider 570 to rod 508. Furthermore, the spacing of slots 564 may corresponding to a length of links 212(1)-212(n) of articulation joint 210 (FIGS. 2A and 2B). In this aspect, advancing or retracting slider 570 and pin 572 relative by one slot 564 in handle 510 may advance or retract rod 508 by one link of the articulation joint in the distal assembly (FIGS. 2A and 2B). Additionally, the position of slider 570 and pin 572 may indicate the position of rod 508 relative to the articulation joint to the operator. For example, track 560 may include the same number of slots 564 as articulation links 212 in articulation joint 210 (FIG. 2B). Furthermore, handle 510 and/or track 560 may include one or more indications 573 (e.g., numerical indications) such that the position of slider 570 and/or pin 572 relative to handle 510 and/or track 560 may indicate the position of rod 508 relative to the articulation joint to the operator.

Figure 6A:
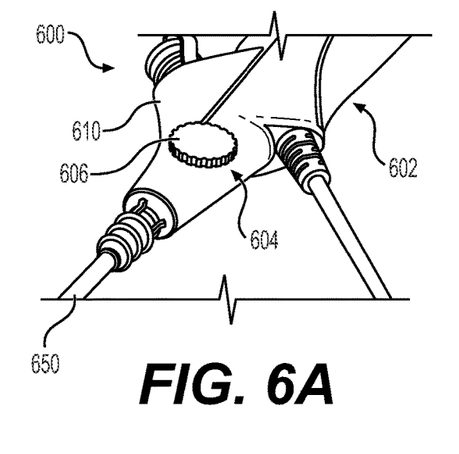
FIGS. 6A and 6B illustrate perspective views of yet another embodiment of the second medical device, with the second medical device coupled to a handle of the first medical device.
Figure 6B:
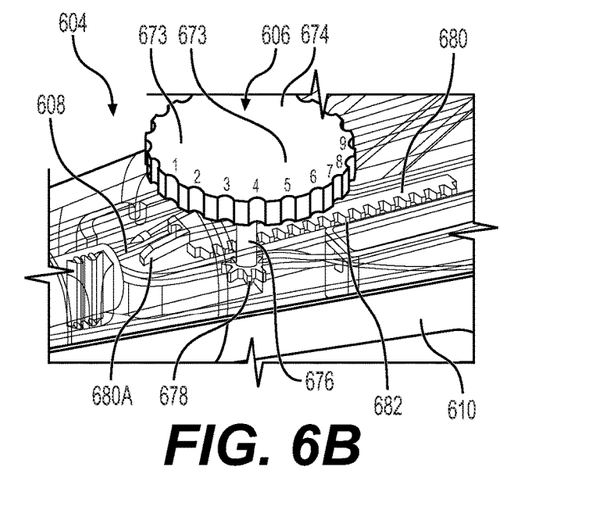

FIGS. 6A and 6B illustrate a portion of another system 600, with elements similar to system 100 shown with 500 added to the element number. FIG. 6A is a perspective view of a portion of system 600, and FIG. 6B is a partially cut-away view of a portion of system 600. System 600 includes a first medical device 602 and a second medical device 604. As discussed above, first medical device 602 includes a handle 610 and a shaft 650. Second medical device 604 includes a control device 606 and a rod 608. In this aspect, control device 606 may be coupled to and/or movable relative to handle 610, for example, a distal portion of handle 610.

As shown in FIGS. 6A and 6B, control device 606 may include a knob or dial 674, for example, including a disc with a plurality of ridges and extensions to form a grip surface. Dial 674 may be connected to a dowel 676 that includes a gear or pinion 678, such that rotation of dial 674 rotates dowel 676 and pinion 678 in the same direction (i.e., clockwise or counterclockwise). Dowel 676 may extend from exterior to handle 610 to interior of handle 610. Control device 606 may also include a rack 680, for example, positioned within handle 610. For example, a distal portion of rack 680 may include a securing portion 680A that secures a rod 608 to rack 680. Additionally, rack 680 includes a plurality of teeth 682, for example, configured to engage with pinion 678.

In this aspect, rotation of dial 674 rotates dowel 676 and pinion 678. Pinion 678 engages with teeth 682 of rack 680, such that rotation of pinion 678 linearly drives rack 680. Accordingly, rotation of dial 674 (clockwise or counterclockwise) linearly drives rack 680 proximally or distally in order to distally extend and/or proximally retract rod 608. Furthermore, the size and/or spacing of pinion 678 and/or teeth 682 may corresponding to a length of links 212(1)-212(n) of articulation joint 210 (FIGS. 2A and 2B). In this aspect, rotating dial 674 to advance or retract rack 680 by one tooth (e.g., one "click") may advance or retract rod 608 by one link of the articulation joint in the distal assembly (FIGS. 2A and 2B). Additionally, dial 674 and/or handle 610 may include one or more indications 673 such that the position of dial 674 relative to handle 610 may indicate the position of rod 608 relative to the articulation joint to the operator.

Figures 7A, 7B, 8:
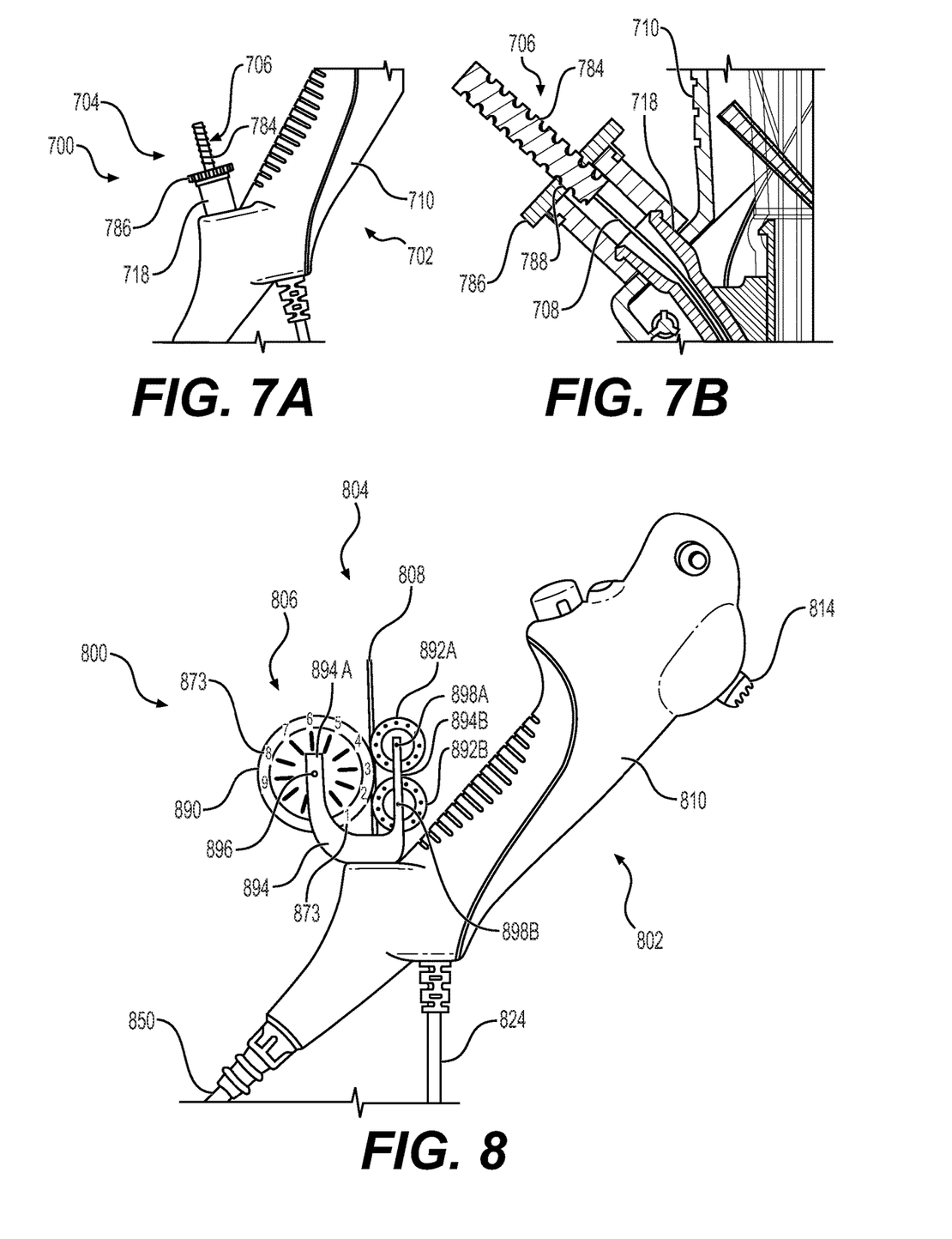
FIGS. 7A and 7B illustrate a side view and a cross-sectional view, respectively, of another embodiment of the second medical device, with the second medical device coupled to the handle of the first medical device.
FIG. 8 illustrates a side view of yet another embodiment of the second medical device, with the second medical device coupled to the handle of the first medical device.

FIGS. 7A and 7B illustrate a portion of another system 700, with elements similar to system 100 shown with 600 added to the element number. FIG. 7A is a side view of a portion of system 700, and FIG. 7B is a lateral cross-sectional view of a portion of system 700. System 700 includes a first medical device 702 and a second medical device 704. As discussed above, first medical device 702 includes a handle 710 and a shaft (not shown). Second medical device 704 includes a control device 706 and a rod 708. In this aspect, control device 706 may be coupled to and/or movable relative to handle 710, for example, a distal portion of handle 710.

As shown in FIGS. 7A and 7B, control device 706 may include a screw 784, for example, including a cylindrical body with a spiral threading. A proximal portion of screw 784 may extend from handle 710 of first medical device 702, and a distal portion of screw 784 may be coupled to a proximal end of rod 708. Additionally, control device 706 may include a coupler 786. Coupler 786 may be coupled to (e.g., fixedly or temporarily mounted on) a portion of handle 710, for example to instrument port 718. Coupler 786 may include an internal threading, for example, corresponding to the threading on screw 784. In this aspect, screw 784 and coupler 786 may form an interface 788.

Rotating screw 784 relative to coupler 786 may advance or retract screw 784 relative to handle 710, and thus distally extend and/or proximally retract rod 708. Furthermore, the size and/or spacing of the threading on screw 784 and/or coupler 786 may corresponding to a length of links 212(1)-212(n) of articulation joint 210 (FIGS. 2A and 2B). In this aspect, rotating screw 784 a certain amount (e.g., a quarter rotation, a half rotation, one rotation, etc.) to advance or retract screw 784 may advance or retract rod 708 by one link of the articulation joint in the distal assembly (FIGS. 2A and 2B). Additionally, screw 784 may be fully unscrewed from coupler 786, for example, to remove screw 784 and rod 708 from first medical device 702. Alternatively or additionally, coupler 786 may be uncoupled (e.g., unscrewed) from instrument port 718, for example, to remove coupler 786, screw 784, and rod 708 from first medical device 702. Furthermore, screw 784 may include one or more indications (not shown) such that the position of screw 784 relative to coupler 786 may indicate the position of rod 708 relative to the articulation joint to the operator.

FIG. 8 illustrates a portion of another system 800, with elements similar to system 100 shown with 700 added to the element number. FIG. 8 is a side view of a portion of system 800. System 800 includes a first medical device 802 and a second medical device 804. As discussed above, first medical device 802 includes a handle 810 and a shaft 850. Handle 810 may include an articulation lever 814, for example, to help control an articulation of a distal portion of shaft 850. Second medical device 804 includes a control device 806 and a rod 808. In this aspect, control device 806 may be coupled to and/or movable relative to handle 810, for example, a distal portion of handle 810.

As shown in FIG. 8, control device 806 may include a primary wheel 890, for example, abutting a proximal portion of rod 808. Control device 806 may also include one or more secondary wheels, for example, two secondary wheels 892A and 892B. Secondary wheels 892A and 892B may abut the proximal portion of rod 808, for example, opposite to primary wheel 890, such that the proximal portion of rod 808 is positioned between primary wheel 890 and secondary wheels 892A, 892B, for example, for three points of contact on rod 808. Primary wheel 890 and secondary wheels 892A, 892B may be coupled to handle 810 via a mounting element 894. In one aspect, mounting element 894 may be coupled to a distal portion of handle 810, for example, opposite to an umbilicus 824, and rod 808 may be delivered through handle 810 and shaft 850 through an instrument port (not shown) or other port. Primary wheel 890 may include a pivot 896 on a first arm 894A of mounting element 894, and secondary wheels 892A, 892B may each include pivots 898A, 898B, respectively, on a second arm 894B of mounting element 894. Although not shown, first arm 894A and second arm 894B may each include two parallel arms. For example, primary wheel 890 may be positioned between parallel arms of first arm 894A, and secondary wheels 892A, 892B may be positioned between parallel arms of second arm 894B.

In this aspect, rotating primary wheel 890 relative to mounting element 894 (clockwise or counterclockwise) may distally extend and/or proximally retract rod 808, for example, via a frictional engagement between primary wheel 890, rod 808, and/or secondary wheels 892A, 892B. Alternatively or additionally, one or more of secondary wheels may be rotated (clockwise or counterclockwise) to extend or retract rod 808 relative to first medical device 802. Furthermore, the size of primary wheel 890, secondary wheels 892A, 892B, and/or mounting element 894 may corresponding to a length of links 212(1)-212(n) of articulation joint 210 (FIGS. 2A and 2B). In this aspect, rotating primary wheel 890 (and/or secondary wheels 892A, 892B) a certain amount (e.g., a quarter rotation, a half rotation, one rotation, etc.) may advance or retract rod 808 by one link of the articulation joint in the distal assembly (FIGS. 2A and 2B). Additionally, primary wheel 890 and/or secondary wheels 892A, 892B may be rotated such that rod 808 is fully removed from first medical device 702. Furthermore, one or more of rod 808, primary wheel 890, and/or secondary wheels 892A, 892B may include one or more indications 873 such that the position of rod 808, primary wheel 890, and/or secondary wheels 892A, 892B, for example, relative to handle 810 may indicate the position of rod 808 relative to the articulation joint to the operator.

Although FIGS. 5A-8 include a single control device and a single rod, this disclosure is not so limited. For example, as discussed above, two or more rods may be delivered through the first medical device, with one or more rods being delivered through one or more of a camera lumen, a working lumen, or a separate lumen of the first medical device. In these aspects, a first control device may be coupled to an instrument port (e.g., FIGS. 6A-8), and a first rod may be delivered through the working lumen. Additionally, a second control device may be coupled to another port (e.g., FIGS. 6A-8) on the handle of the first medical device, and the second rod may be delivered through another lumen (e.g., a camera lumen or a separate lumen). In another aspect, the two or more rods may be delivered through the same lumen. In these aspects, the two or more rods may be separately manipulated and positioned at various positions within the lumen(s).

In another aspect, a first control device may be integrated into the handle of the first medical device (e.g., FIGS. 5A-5B), and a first rod may be delivered through the working lumen. Additionally, a second control device may be integrated into the handle of the first medical device (e.g., FIGS. 5A-5B), and the second rod may be delivered through another lumen (e.g., a camera lumen or a separate lumen). In another aspect, the two or more rods may be delivered through the same lumen. Furthermore, in another aspect, two rods may be delivered through the instrument port. In this aspect, two control devices may be adjacent to and/or coupled to the instrument port. In these aspects, the two or more rods may be separately manipulated and positioned at various positions within the lumen(s). Alternatively, two or more rods may be coupled to a single control device, with the two or more rods limiting the articulation of articulation joint 210 by a greater amount than a single rod.

Figure 9:
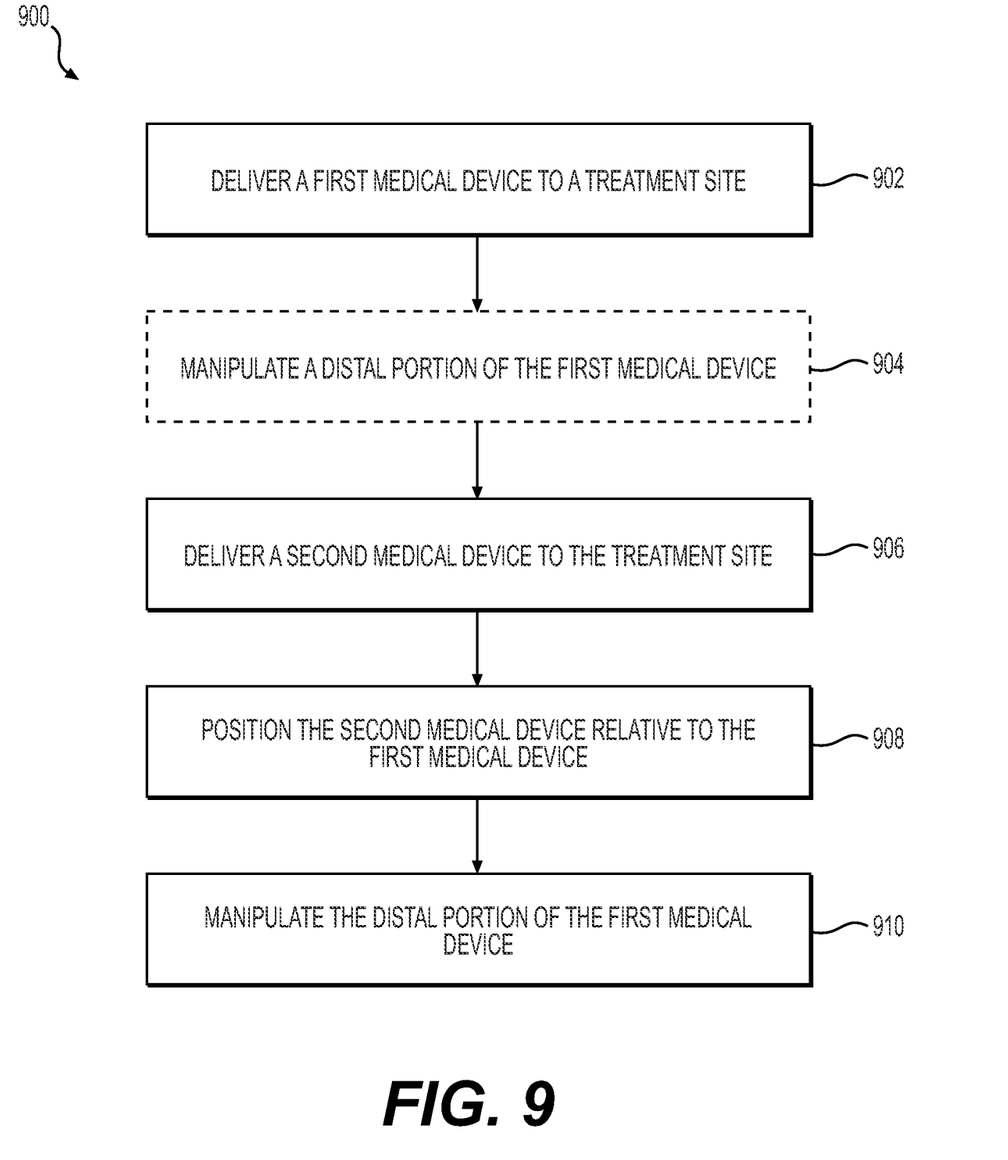
FIG. 9 is a flow diagram of an exemplary method, according to aspects of this disclosure.

FIG. 9 illustrates a method 900 that may be performed with any of medical systems 100, 500, 600, 700, and 800. A step 902 includes delivering a first medical device (e.g., first medical device 102, 502, 602, 702, or 802) to a treatment site. Delivering the first medical device to the treatment site may include delivering a shaft (e.g., shaft 150, 650, or 850) including a distal assembly (e.g., distal assembly 152) with an articulation joint (e.g., articulation joint 210).

Next, an optional step 904 includes manipulating a distal portion of the first medical device. Step 904 may include manipulating actuation lever 114 on handle 110 to deflect or articulate distal assembly 152. For example, manipulating actuation lever 114 may manipulate articulation wires 240 to articulate articulation joint 210 (e.g., through an articulation angle shown by the dashed lines of distal assembly 152 in FIGS. 4A-4D). Optionally, step 904 may also include performing a first medical procedure, for example, with an instrument delivered through a working lumen of the first medical device. Alternatively, method 900 may not include step 904, and may instead proceed from step 902 to step 906.

A step 906 includes delivering a second medical device (e.g., second medical device 104, 504, 604, 704, or 804) to the treatment site. Step 906 includes delivering the second medical device through a lumen (e.g., a camera lumen, a working lumen, or a separate lumen) of the first medical device. For example, as discussed above, step 906 may include delivering a rod (e.g., rod 108, 508, 608, 708, or 808) through an instrument port on a handle of the first medical device. In these aspects, step 906 may include delivering the rod to a distal portion of the first medical device, for example, to a distal assembly (e.g., distal assembly 152) or to an articulation joint (e.g., articulation joint 210) of the first medical device. In this step, delivering the second medical device to the treatment site may include delivering the second medical device through the lumen of the first medical device to a distal portion of the first medical device. That is, the second medical device may be positioned proximal of the distal end of the first medical device. Nevertheless, the second medical device may be positioned proximate to the treatment site. Delivering the rod to a distal portion of the first medical device may allow the user to articulate the distal portion of the first medical device (i.e., distal assembly 152) through a smaller articulation radius, for example, for smaller or more precise adjustments with less sensitivity to movements of articulation lever 114.

In one or more aspects, a step 908 may include positioning the second medical device relative to the first medical device. For example, as discussed above, the second medical device may include a control device to control a longitudinal position of the rod. As discussed above, the control device may linearly adjust the position of the rod. For example, the control device may include a slider 570 with a pin 572 that is movable within a track 560, for example, in a handle of the first medical device, as discussed with respect to FIGS. 5A and 5B. Alternatively, the control device may include a dial 674, pinion 678, and rack 680, as discussed with respect to FIGS. 6A and 6B. In another aspect, the control device may include screw 784 and coupler 786, as discussed with respect to FIGS. 7A and 7B. Furthermore, in another aspect, the control device may include primary wheel 890, one or more secondary wheels 892A, 892B, and/or mounting element 894, as discussed with respect to FIG. 8.

Furthermore, a step 910 may include manipulating the distal portion of the first medical device. Step 910 may include manipulating actuation lever 114 on handle 110 to deflect or articulate distal assembly 152. For example, manipulating actuation lever 114 may manipulate articulation wires 240 to articulate articulation joint 210 (e.g., through an articulation angle shown by the solid lines of distal assembly 152 in FIGS. 4A-4D). In these aspects, articulation joint may articulate by a smaller articulation angle with the second medical device positioned within the first medical device, compared to an articulation angle of the first medical device in step 904. For example, as discussed above with respect to FIGS. 4A-4E, the second medical device may adjust (e.g., reduce) the articulation angle of distal assembly 152. Optionally, step 910 may also include performing a second medical procedure, for example, with an instrument delivered through a working lumen of the first medical device.

Furthermore, method 900 may include an optional step of removing the second medical device from the lumen of the first medical device. With the second medical device removed, the first medical device may articulate through the full range of the first articulation angle range (e.g., through an articulation angle shown by the dashed lines of distal assembly 152 in FIGS. 4A-4D). Additionally, the second medical device may be repositioned (e.g., retracted or extended through various links 212 of articulation join 210, via the control device) and/or removed from the lumen of the first medical device 102 as many times as necessary during a procedure.

The systems, devices, and methods discussed herein may allow for variable deflection and/or articulation of a shaft or distal assembly of a medical device. For example, different procedures and/or different bodily cavities or lumens with a patient may require different maneuvers and/or different articulation radii. As discussed herein, positioning the second medical device within a lumen of the first medical device the user to adjust the articulation radii and/or articulation angle of the first medical device, without the need for a separate guidewire or other element. Furthermore, positioning the second medical device within portions of the first medical device may allow for different angles or radii of articulation. Additionally, positioning the second medical device within portions of the first medical device may reduce the overall sensitivity of articulation or deflection, such that inadvertent manipulation of the articulation lever is less likely to inadvertently cause the shaft or distal assembly to contact unintended portions of the body cavity or lumen. Aspects of this disclosure may help the user manipulate a distal end of a medical device (e.g., distal assembly 152 of first medical device 102) in order to traverse various cavities and/or lumens. For example, aspects of this disclosure may help the user manipulate the distal end of the medical device in order to traverse and/or transition between portions of the larynx, trachea, bronchi (primary bronchi), lobar (secondary bronchi), segmental (tertiary bronchi), bronchiore, terminal bronchiore, or any other portion of the respiratory system.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems, catheters, elongate instruments, or other scopes such as colonoscopes, bronchoscopes, ureteroscopes, duodenoscopes, etc., or other types of imagers. It also should also be understood that one or more aspects of any of the medical devices described herein may be used for sensing, monitoring, or otherwise treating tissue in any part of the human body. For example any of the medical devices described herein may be used in medical procedures such as for endoscopic cholangio-pancreatography, colonoscopies, cancer screening, examination of mucinous lesions, and/or other procedures where removal and/or detection of the type of tissue is needed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical system, comprising:
   a first medical device, wherein the first medical device includes:
   a handle;
   a shaft, wherein the shaft includes a lumen, wherein a distal portion of the shaft includes an articulation joint, and wherein the lumen extends through at least a portion of the articulation joint; and
   one or more articulation wires extending at least partially through the articulation joint, wherein the one or more articulation wires are configured to articulate the articulation joint; and;
   a second medical device, wherein the second medical device includes:
   a control device; and
   a rod,
   wherein the rod is selectively positionable within at least a portion of the lumen of the shaft within the articulation joint, wherein the control device is configured to control a position of the rod within the shaft, and wherein the position of the rod within the shaft controls an articulation angle of the articulation joint.

2. The medical system of claim 1, wherein the control device is integrated in or coupled to a portion of the handle.

3. The medical system of claim 2, wherein the control device includes a slider, a pin coupled to the slider, and a track positioned within a distal portion of the handle, and wherein movement of the pin within the track controls the position of the rod within the lumen of the shaft.

4. The medical system of claim 3, wherein the track includes a central channel, a plurality of slots extending from the central channel, and a plurality of grooves extending from the slots.

5. The medical system of claim 4, wherein a spacing of the slots along the central channel corresponds to a length of one or more links in the articulation joint.

6. The medical system of claim 1, wherein the control device includes a dial, a dowel extending from the dial, and a pinion coupled to the dowel, and wherein the rod is coupled to a rack.

7. The medical system of claim 6, wherein rotational movement of the dial actuates a linear movement of the rack to control the position of the rod within the shaft.

8. The medical system of claim 7, wherein the rack includes a plurality of teeth, and wherein a spacing of the teeth on the rack corresponds to a length of one or more links in the articulation joint.

9. The medical system of claim 1, wherein the control device includes a screw coupled to the rod and a coupler, wherein the screw includes a threading, wherein the coupler includes an internal threading, and wherein the rod is coupled to a distal end of the screw.

10. The medical system of claim 9, wherein rotational movement of the screw controls the position of the rod within the shaft.

11. The medical system of claim 1, wherein the control device includes a primary wheel, one or more secondary wheels, and a mounting element, wherein the mounting element is coupled to a distal portion of the handle.

12. The medical system of claim 11, wherein rotational movement of the primary wheel or the one or more secondary wheels controls the position of the rod within the shaft.

13. The medical system of claim 1, wherein the articulation joint includes nine articulation links, and wherein each articulation link provides for 25 degrees of articulation.

14. The medical system of claim 1, wherein the rod is less flexible than the articulation joint, wherein the articulation joint includes a plurality of articulation links, and wherein more distal articulation links provide for greater articulation than more proximal articulation links.

15. The medical system of claim 1, wherein the handle includes an instrument port on a distal portion of the handle configured to receive the rod and to guide the rod into the lumen of the shaft, wherein the first medical device includes an articulation lever positioned on a portion of the handle, and wherein the articulation lever is connected to the articulation joint via the one or more articulation wires.

16. A medical system, comprising:
a first medical device, wherein the first medical device includes:
a handle;
a shaft, wherein the shaft includes a plurality of lumens, wherein a distal portion of the shaft includes an articulation joint having a plurality of links; and,
a second medical device, wherein the second medical device includes:
a control device; and
a rod,
wherein the rod is configured to transition from a first configuration, in which the rod extends through a first number of the plurality of links to a second configuration, in which the rod extends through a second number of the plurality of links
wherein the first number is greater than the first number; and
wherein, in the second configuration, the articulation joint is deflectable by a greater angle than in the first configuration.

17. The medical system of claim 16, wherein the first medical device includes a plurality of articulation wires extending through at least some of the plurality of links, and wherein actuation of the articulation wires deflects the articulation joint.

18. The medical system of claim 16, wherein the control device is integrated in or coupled to a portion of the handle.

19. A medical system, comprising:
a first medical device, wherein the first medical device includes:
a handle;
a shaft, wherein the shaft includes a lumen, wherein a distal portion of the shaft includes an articulation joint, and wherein the lumen extends through at least a portion of the articulation joint; and
one or more articulation wires configured to articulate the articulation joint; and;
a second medical device, wherein the second medical device includes:
a control device; and
a rod,
wherein the rod is selectively positionable within at least a portion of the lumen of the shaft within the articulation joint, wherein the control device is configured to control a position of the rod within the shaft, and wherein a portion of the articulation joint that is proximal to a distal end of the rod has a greater stiffness than a portion of the articulation joint that is distal to the distal end of the rod such that the rod controls an angle at which the articulation wires articulate the articulation joint.

20. The medical system of claim 19, wherein distal movement of the rod decreases the angle.

\* \* \* \* \*